(12) United States Patent
Jaroch

(10) Patent No.: US 11,100,177 B2
(45) Date of Patent: Aug. 24, 2021

(54) INSTRUMENTED RESEARCH AGGREGATION SYSTEM

(71) Applicant: Colossio, Inc., Chicago, IL (US)

(72) Inventor: Joseph A. Jaroch, Chicago, IL (US)

(73) Assignee: Colossio, Inc., Chicago, IL (US)

( * ) Notice: Subject to any disclaimer, the term of this patent is extended or adjusted under 35 U.S.C. 154(b) by 386 days.

(21) Appl. No.: 15/900,076

(22) Filed: Feb. 20, 2018

(65) Prior Publication Data
US 2019/0258740 A1 Aug. 22, 2019

(51) Int. Cl.
*G06F 16/9535* (2019.01)
*G16H 10/60* (2018.01)
*G06F 16/93* (2019.01)
*G06F 16/2457* (2019.01)

(52) U.S. Cl.
CPC .... *G06F 16/9535* (2019.01); *G06F 16/24578* (2019.01); *G06F 16/93* (2019.01); *G16H 10/60* (2018.01)

(58) Field of Classification Search
CPC .............. G06F 16/9535; G06F 16/93; G06F 16/24578; G06F 16/951; G16H 10/60; G16H 70/20
See application file for complete search history.

(56) References Cited

U.S. PATENT DOCUMENTS

| | | | | |
|---|---|---|---|---|
| 7,174,332 B2* | 2/2007 | Baxter | ................ | G06F 11/1435 |
| 8,849,878 B1* | 9/2014 | Bachu | .................. | G06F 21/602 |
| | | | | 707/823 |
| 2008/0228695 A1* | 9/2008 | Sifry | ....................... | H04L 67/26 |
| 2013/0268524 A1* | 10/2013 | Etkin | .................... | G06F 16/903 |
| | | | | 707/723 |
| 2014/0067847 A1* | 3/2014 | Barbieri | ............... | G06F 19/324 |
| | | | | 707/765 |
| 2016/0205207 A1* | 7/2016 | Backstrom | ............. | H04L 67/22 |
| | | | | 709/224 |

* cited by examiner

*Primary Examiner* — Albert M Phillips, III
(74) *Attorney, Agent, or Firm* — Barnes & Thornburg LLP

(57) ABSTRACT

A system and methods for instrumented research aggregation of content are provided. Crawling processes having multiple instances and multiple IP regions per instance are distributed to multiple processors for a variety of designated content sources and feeds. An aggregated content database is generated and trigger parameters and/or subscriptions are set in relation to the database. As new content is posted to the designated content sources and feeds, a full copy of the content document is downloaded and stored, raw text is extracted from the stored document and stored, and content analysis is performed on the text document and the results are stored. For any new content that trips the set triggers/subscription parameters, a notification is sent to the associated users with a link to the stored document and an abstract of relevant text.

16 Claims, 9 Drawing Sheets

INSTRUMENTED RESEARCH AGGREGATION SYSTEM

TECHNICAL FIELD

The present disclosure generally relates to research systems, and more specifically relates to an instrumented research aggregation system for aggregating posted content and presenting to a research user published articles representing significant statistical matches to the user's input interests.

BACKGROUND

The internet has allowed for a significant increase in communication speed which has shown to be very beneficial to forward progress, breaking down barriers of time and distance. Scientists, researchers, and other academics historically needed to rely on mail correspondence which was notoriously slow. Published papers had limited circulation and scientific progress was limited by the lack of ease of access to information.

Today, these problems are significantly reduced. However, with the relatively low friction of academic publishing comes another side of increased friction, namely being overwhelmed with information. There is incredible research being performed in a large number of fields and a constant stream of publications produced, but wading through these publications to keep apprised of the latest developments in a given field is extremely time consuming and challenging.

It is desired to provide a system for efficiently monitoring publication sources, obtaining primary concepts based on identified publications, and providing users with relevant content based on matches with user-supplied concepts.

The description provided in the background section should not be assumed to be prior art merely because it is mentioned in or associated with the background section. The background section may include information that describes one or more aspects of the subject technology.

SUMMARY

According to certain aspects of the present disclosure, a computer-implemented method for providing instrumented research aggregation results is provided. In one or more embodiments, the method includes providing, to one or more servers, a set of content sources and initiating, by the one or more servers, a plurality of crawling instances, each crawling instance associated with a plurality of Internet Protocol (IP) addresses. The method also includes generating, on the one or more servers, an aggregated content database based on the plurality of crawling instances and identifying, by a first crawling instance, a new content document on a first content source, wherein the new content document is newly published and is not currently in the aggregated content database. The method further includes downloading and storing in the aggregated content database, by the one or more servers, a copy of the new content document and a link back to the original new content document on the first content source. The method also includes extracting, by the one or more servers, text content from the new content document and storing, in the aggregated content database, the extracted text content as a text document, wherein the text document is associated with the new content document. The method further includes executing, by the one or more servers, a content analysis of the text document, storing, in the aggregated content database, content analysis results of the content analysis, wherein the content analysis results are associated with the text document, and providing initial information related to the new content document based on one or more user inputs.

According to certain aspects of the present disclosure, an instrumented research aggregation system is provided. The system includes a memory and a processor configured to execute instructions. The executed instructions cause the processor to receive a set of content sources; initiate a plurality of crawling instances, each crawling instance associated with a plurality of Internet Protocol (IP) addresses, wherein two or more of the plurality of crawling instances share one or more of the IP addresses; generate an aggregated content database based on the plurality of crawling instances; identify, from a first crawling instance, a new content document on a first content source, wherein the new content document is newly published and is not currently in the aggregated content database; download and store in the aggregated content database a copy of the new content document; extract text content from the new content document; store, in the aggregated content database, the extracted text content as a text document, wherein the text document is associated with the new content document; execute content analysis of the text document; store, in the aggregated content database, content analysis results of the content analysis, wherein the content analysis results are associated with the text document; and provide initial information related to the new content document based on one or more user inputs.

According to certain aspects of the present disclosure, a non-transitory machine-readable storage medium comprising machine-readable instructions for causing a processor to execute a method for providing instrumented research aggregation results is provided. The method includes generating an aggregated content database based on a plurality of crawling instances, wherein the aggregated content database comprises a plurality of content documents, a plurality of text documents and a plurality of content analysis results, each content document being associated with one of the plurality of text documents and one of the plurality of content analysis results; identifying, by a first crawling instance, a new content document on a first content source, wherein the new content document is newly published and is not currently in the aggregated content database; downloading and storing in the aggregated content database a copy of the new content document and a link back to the original new content document on the first content source; generating a text document from the new content document; storing, in the aggregated content database, the text document, wherein the text document is associated with the new content document; performing content analysis of the text document; storing, in the aggregated content database, content analysis results from the content analysis, wherein the content analysis results are associated with the new content document; and providing initial information related to the new content document based on one or more user inputs.

It is understood that other configurations of the subject technology will become readily apparent to those skilled in the art from the following detailed description, wherein various configurations of the subject technology are shown and described by way of illustration. As will be realized, the subject technology is capable of other and different configurations, and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

Figure 1:
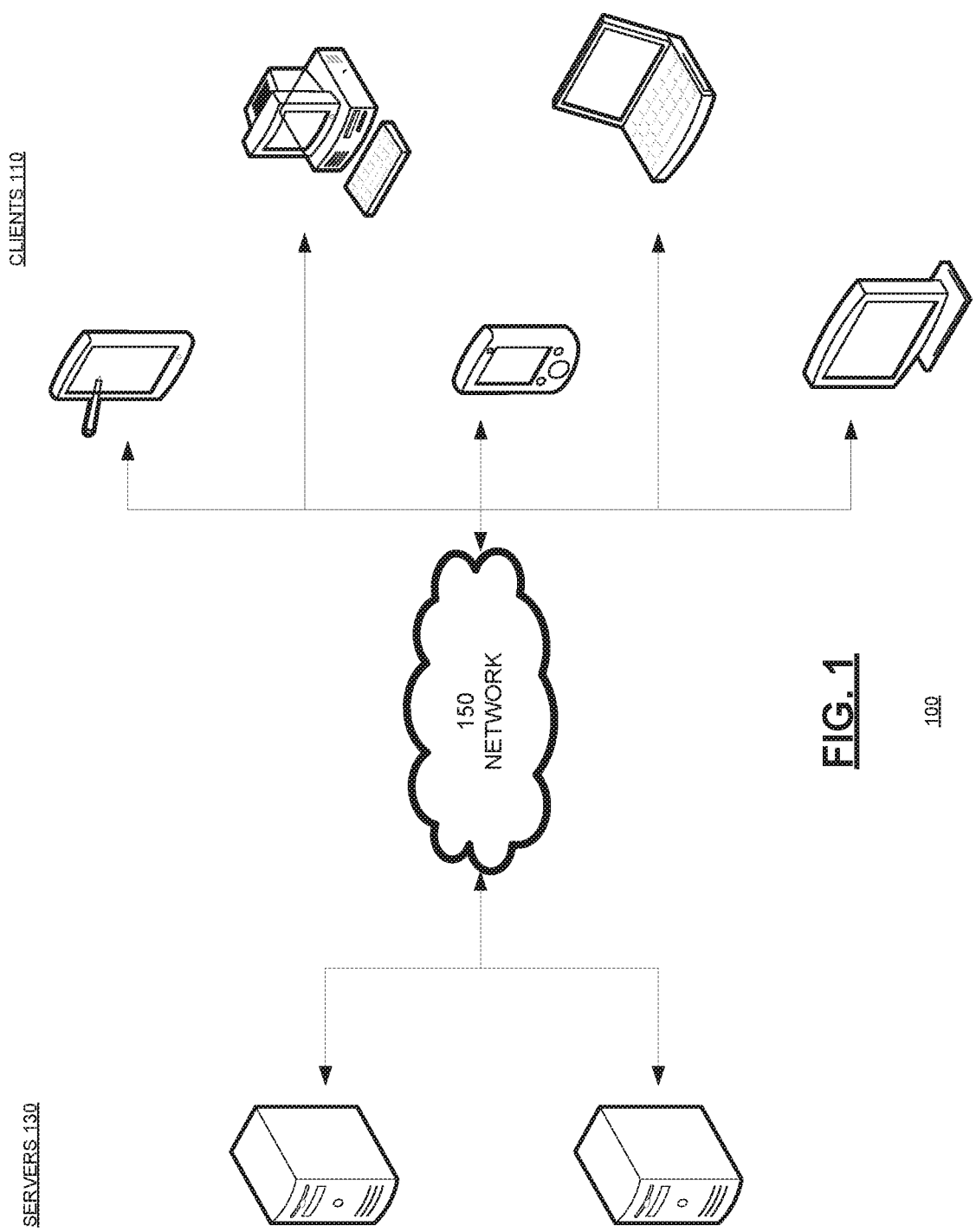
FIG. 1 illustrates an example architecture for providing an instrumented research aggregation system.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

General Overview

In a conventional academic research system, it is necessary to pull each article, research paper, or publication related to a given field for which the user is interested in exploring. The user generally must spend hours manually reading through each article to identify if it is relevant to the user's needs or searching the entire article for specific terms and then reviewing the context of the text around each identified term for its relevance to the user's interest.

The present disclosure overcomes conventional issues by inverting the model. Rather than needing to pull each article, research paper, or publication related to a given field, the disclosed instrumented academic research system aggregates all of the content posted from a variety of sources and pushes articles to the reader only when they represent significant statistical matches. This reduces the number of articles needed to be read and ensures that important papers are not missed in the noise of all of the published content.

Thus, in one or more embodiments, the disclosed system monitors a variety of different sources where articles are published, regularly refreshing the source RSS feeds and/or checking for changes in a file repository. An alert application may be created to monitor other websites and web crawling may be performed to track other sources automatically. As each new published article is identified, it is downloaded and the content is extracted to save the article as plain text. For example, a conventional PDF-to-text tool may be used to obtain a plain text version of the downloaded article.

Each article may then be processed to obtain an output of primary concepts within the article. For example, a plain text article may be passed through a non-linguistic content analysis system, such as that described in commonly owned U.S. patent application Ser. No. 15/679,714 filed Aug. 17, 2017, and entitled "Non-Linguistic Content Analysis System," which is herein incorporated by reference in its entirety.

A database of user-supplied concepts may then be queried to identify if any users are monitoring one of the subjects pertaining to the newly downloaded article. For example, a user may provide a list of concepts for which the user is interested in obtaining further information. These concepts may be broad subjects or very narrow and specific terms. For example, the breadth and applicability of each concept may vary depending on the subject matter.

The end result is a significant bandwidth efficiency gain being that each article needs to only be downloaded once for the entire user base. Further, users do not need to spend hours manually reading through each article to identify if it is relevant to their needs. The present system also eliminates the need for the entirety of each paper or article to be searched for each term as only the pre-determined most relevant terms are returned. For example, papers that only passively mention a particular concept will not be included when the user is looking for papers that significantly refer to a particular concept.

There are multiple discrete use cases for the subject technology. Here, monitoring academic research and identifying important concepts in each paper allows for researchers to efficiently parse through large volumes of published papers. In the medical field for example, the subject technology may be implemented within an electronic medical record (EMR) system to automatically notify a physician about newly published studies and research that pertains to an individual patient. As another example, the subject technology may also be used to aggregate information when exploring a new subject, thereby pulling in relevant information from a variety of sources to display in a single panel for an end user.

In one or more embodiments, a server-side crawler may be given a set of sources that represent a superset of available research categories. The set of sources may include academic paper portals like popular academic journals, search engines, pre-print servers, news media and any other sources. The set of sources may also include publicly available databases, knowledge bases or similar resources. Thus, the subject technology may operate in a source-agnostic manner, taking data from any input or combination of sources.

Crawling sources may be spread across multiple discrete instances and a range of discrete Internet Protocol (IP) addresses to ensure that downloads will succeed. Thus, different crawling sources may share the same IP addresses as they won't be subject to rate limitations when querying different services.

Some sources may include Rich Site Summary (RSS) feeds, for which each RSS feed may be used to identify when content is published. Other mechanisms may be used for identifying new content as well. For example, other mechanisms such as checking the timestamp of a file repository, incrementing the index of a filename (e.g., file1.pdf, file2.pdf, file3.pdf, . . . filen.pdf), and/or downloading webpage content and comparing it against previously downloaded content to identify differences and follow new links.

The ultimate result of this crawling process will generally be a document in a standard format (e.g., PDF, Word, or LaTeX). Regardless of the format, each document obtained from the crawling process is stored in its entirety within the database along with a link back to where the document originated. Thus, only a single one-time download is required for each new document that is identified.

Each obtained document may then be passed into a separate thread for asynchronous processing, thus ensuring that the processing overhead for any individual document does not negatively impact the performance of the collection of all documents. Thus, each document is run through a processing tool to extract text based on its format. For example, standard PDF-to-text, DOC-to-text and/or LaTeX-to-text tools may be used to extract the raw text based on the format of the document.

After the obtained document is processed, the raw extracted text is stored in the database alongside the downloaded source document. Further, in each thread, the raw text is passed through context analysis and the output is stored in the database. For example, the Non-Linguistic Content Analysis System discussed above may be used to generate relevant concepts from the document.

The output (e.g., relevant concepts) from the content analysis may be iterated over and compared against a database of user-supplied trigger concepts. If a concept in the newly encountered document (e.g., paper) has been marked to be triggered upon or subscribed to by a user, an appropriate notification may be sent. For example, notification may include any of sending an email, sending a text/short message service (SMS) message and sending an output for display on a dashboard.

A link to the original content may be provided to the user. In addition, a snippet of an abstract of the document may be provided with the link if an abstract is provided in the document. The user may then perform further filtering of the link and/or abstract snippet in order to decide whether or not to download and read the full paper or document.

In one or more embodiments, the subject technology may include integration into one or more EMR systems. For example, when new patient treatment data is entered into a third party EMR system, the data may be stripped of personally identifiable information and a unique identifier may be generated for the particular case. Thus, the data may be anonymized to prevent identification of any particular individual in compliance with privacy and health laws or processes.

The treatment data may be compared against previously collected treatment data from this particular EMR record. If the new treatment data has not been seen before, a query may then be produced. For example, a query may be produced that includes the new treatment data as a plaintext string (e.g., "ibuprofen") and an identifier (ID) for this record (e.g., "10122").

A server may then receive the query (e.g., request) and automatically create a subscription for the string. Then, if the server encounters a new paper, study or body of research that has a concept identified from the content analysis that matches the subscribed string, the physician may then be notified with a link to the paper and information on any matching record identifiers.

The subject technology allows a physician to keep apprised of any new research pertaining to treatments that the physician is prescribing without the physician or a member of the physician's staff needing to manually pore over all published research in an attempt to stay up to date. Further, the relationship between treatment and record ID allows the physician to immediately know which patients are impacted by new research so that the physician can proactively review existing patient cases and adjust treatment accordingly.

In one or more embodiments, the subject technology may be implemented for tailored or curated education and learning on a particular subject. Here, the system does not push information out to the user, but instead produces a curated view into a subject from already-held knowledge within the server.

For example, a user may enter a starting keyword or phrase (e.g., "physics"). Then, rather than processing the keyword like a search engine where the word is searched across stored copies of webpages, the system identifies papers and content most related to the keyword. Here, to ensure information is introduced in a logical sequence for learning (e.g., introducing less complex information first, then progressively introducing more complicated topics), an assessment system may be used to filter matching documents and matching portions of documents. For example, an assessment system may be used as described in commonly owned U.S. patent application Ser. No. 15/729,098 filed Oct. 10, 2017, and entitled "Automated Quantitative Assessment Of Text Complexity," which is herein incorporated by reference in its entirety.

An identified papers or content will likely have other, related topics (e.g., "Einstein"). These related topics may be pulled in to the output, allowing the user to move from the starting, highest level category (e.g., "physics") through to the related categories (e.g., "Einstein").

Here, the most relevant portions of a matching document may be used rather than the entire document in most cases. The most relevant portions of a document may be identified via an information inspection system. For example, an information inspection system may be used as described in commonly owned U.S. patent application Ser. No. 15/680,788 filed Aug. 18, 2017, and entitled "Information Density Of Documents," which is herein incorporated by reference in its entirety.

The process may continue as the user navigates a received page, pulling in additional content at deeper levels as the user learns about the subject. Here, all output may be retained on the single page rather than just being presented as a portal (e.g., list of links) to navigate to other pages as provided by conventional search engines. Thus, the results presented as output to the user are more comparable to a textbook and provide for a fluid learning process, as opposed to the typical process of having to click on many different webpages and opening different tabs to attempt to gather information that is even remotely relevant to the user's interest.

In one or more embodiments, the subject technology may be implemented for corporate content ingestion. Similar to embodiments discussed above, corporate content ingestion system may act as a portal into corporate data, leveraging the same metadata throughout the enterprise. For example, the above-mentioned web-crawling technology may be deployed on a local server or fileshare within a corporation, collecting documents and extracting text in the same manner as if the documents were webpages, then indexing the extracted text documents as discrete documents rather than as external links. Key concepts may then be extracted from each document, such as by the Non-Linguistic Content Analysis System discussed above.

A user may then enter a starting keyword or phrase (e.g., "user experience toolkit"). In this example, the system may then identify all content within the organization pertaining to the phrase "user experience toolkit," showing the lowest text complexity content first and progressing through to more complex content. Such an ordered showing may result in introductory user guides being shown before technical documentation, which are both shown before raw source code, for example.

The user may use this search to learn about internal information held by the company and to further expand the user's understanding of a subject based on internal documentation. The user may also subscribe to content via their keyword phrase, thus being automatically notified when new content is created that substantially pertains to the user's initial query.

Example System Architecture

Architecturally, the representative technology can be deployed anywhere. For example, it may be preferable to operate on a very powerful server, in particular one with parallel processing capabilities. When used in the cloud for monitoring research and content, the system may be deployed with a central database, which may leverage a network of other servers with discrete IP addresses to spread the load of downloading new content. Users may access the system either via a webpage or via an application programming interface (API) implemented within an existing system (e.g., within an EMIR system used by a physician to automatically populate subscriptions to new patient data).

In one or more embodiments, the system may be deployed on a very powerful server, in particular one with parallel processing capabilities. Graphics cards may be used as optimizations for processing more operations in parallel. In one or more aspects, the generated workload may be optimally distributed across multiple different physical computers.

FIG. 1 illustrates an example architecture 100 for aggregating posted content and providing the most statistically relevant content associated with user inputs. The architecture 100 includes servers 130 and clients 110 connected over a network 150.

The clients 110 can be, for example, desktop computers, mobile computers, tablet computers (e.g., including e-book readers), mobile devices (e.g., a smartphone or personal digital assistant), set top boxes (e.g., for a television), video game consoles, or any other devices having appropriate processor, memory, and communications capabilities for querying, storing and/or analyzing content data. The system aggregates posted content from any combination of servers 130 and clients 110 over the network 150, stores the gathered content on a database on one or more servers 130, and processes the content to obtain and store extracted text in the database.

One or more of the many servers 130 are configured to analyze the extracted text content and store the analysis results in the database. The database may include, for each content item in the database, information on the relevance or weight of the content item with regards to user input received from a client 110. The database on the servers 130 can be queried by clients 110 over the network 150. For purposes of load balancing, multiple servers 130 can host the database either individually or in portions.

The servers 130 can be any device having an appropriate processor, memory, and communications capability for hosting an instrumented research aggregation application and database. The network 150 can include, for example, any one or more of a personal area network (PAN), a local area network (LAN), a campus area network (CAN), a metropolitan area network (MAN), a wide area network (WAN), a broadband network (BBN), the Internet, and the like. Further, the network 150 can include, but is not limited to, any one or more of the following network topologies, including a bus network, a star network, a ring network, a mesh network, a star-bus network, tree or hierarchical network, and the like.

Example System for Instrumented Research Aggregation and Notification

Figure 2:
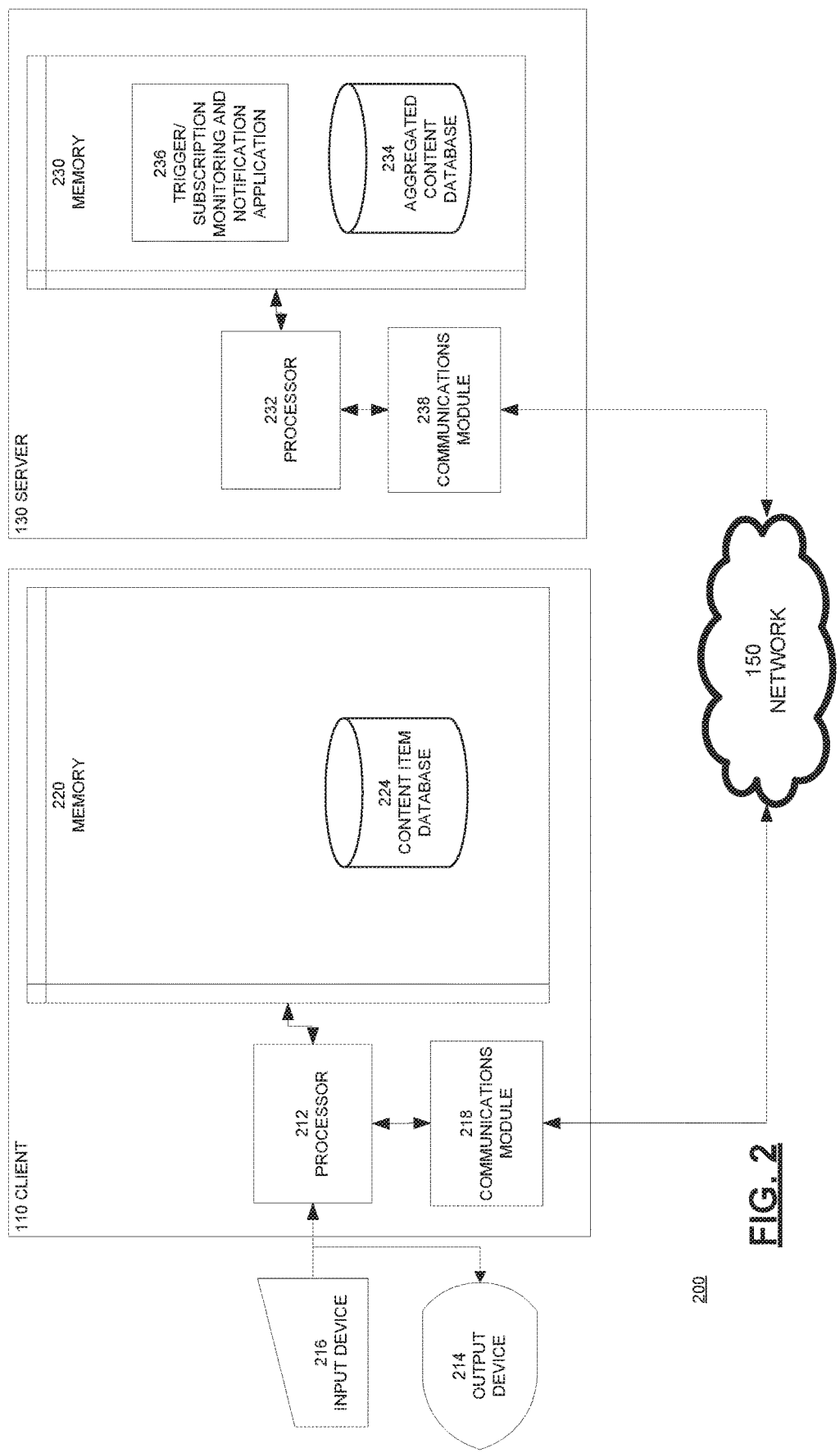
FIG. 2 is a block diagram illustrating an example client and server from the architecture of FIG. 1 according to certain aspects of the disclosure.

FIG. 2 is a block diagram 200 illustrating an example server 130 and client 110 in the architecture 100 of FIG. 1 according to certain aspects of the disclosure.

The client 110 and the server 130 are connected over the network 150 via respective communications modules 218 and 238. The communications modules 218 and 238 are configured to interface with the network 150 to send and receive information, such as data, requests, responses, tools and commands to other devices on the network. The communications modules 218 and 238 can be, for example, modems or Ethernet cards. The client 110 also includes an input device 216, such as a stylus, touchscreen, keyboard, or mouse, and an output device 214, such as a display. The server 130 includes a processor 232, the communications module 238, and a memory 230. The memory 230 includes an aggregated content database 234 and a trigger/subscription monitoring and notification application 236.

The client 110 further includes a processor 212, the communications module 218, and a memory 220. The memory 220 includes a content item database 224. The content item database 224 may include, for example, a link to an original content document and a snippet of an abstract of the content document, each which may be interacted with by a user of the client 110. The content item database 224 may also include a full copy of the original content document. The client 110 may be configured to initiate one or more user inputs related to a content item from the content item database 224, querying the aggregated content database 234 on the server 130 for additional content relevant to the user inputs, and receiving and storing relevant links and abstracts received from the trigger/subscription monitoring and notification application 236 on the server 130.

The processors 212, 232 of the client 110, server 130 are configured to execute instructions, such as instructions physically coded into the processor 212, 232 instructions received from software in memory 220, 230 or a combination of both. For example, the processor 212 of the client 110 may execute instructions to generate a query to the server 130 for content items based on user inputs, to receive content from the server 130, to store the received content in the content item database 224, and to provide the content for display on the client 110. The processor 232 of the server 130 may execute instructions to find and store new content to the aggregated content database 234, to extract a text file from the new content and store the extracted text file in the aggregated content database 234, to analyze the text file and store the results in the aggregated content database 234, and to provide the most relevant content to the client 110. The client 110 is configured to request and receive relevant content to/from the server 130 over the network 150 using the respective communications modules 218 and 238 of the client 110 and server 130.

Specifically, the processor 212 of the client 110 executes instructions causing the processor 212 to receive user input (e.g., using the input device 216) to generate a query out to other devices through the network 150 and to store received content data within the content item database 224. For example, the user may type in specific words or concepts of interest on the client 110, which then generates a query out to any resources on the network 150.

The processor 232 of the server 130 may receive from the client 110 a set of user inputs to use in monitoring for new relevant content or as the basis for a client subscription. The processor 232 of the server 130 may execute the trigger/subscription monitoring and notification application 236 over the inputs provided by the client (e.g., researcher). The processor 232 of the server 130 may then execute the trigger/subscription monitoring and notification application 236 to continuously monitor newly posted content from various sources and provide links and/or abstract snippets of the most relevant content to the client 110.

The techniques described herein may be implemented as method(s) that are performed by physical computing device(s); as one or more non-transitory computer-readable storage media storing instructions which, when executed by computing device(s), cause performance of the method(s); or, as physical computing device(s) that are specially configured with a combination of hardware and software that causes performance of the method(s).

FIGS. 3-8 illustrate example processes 300-800 of an instrumented research aggregation system using the example server 130 of FIG. 2. While FIGS. 3-8 are described with reference to FIG. 2, it should be noted that the process steps of FIGS. 3-8 may be performed by other systems.

Figure 3:
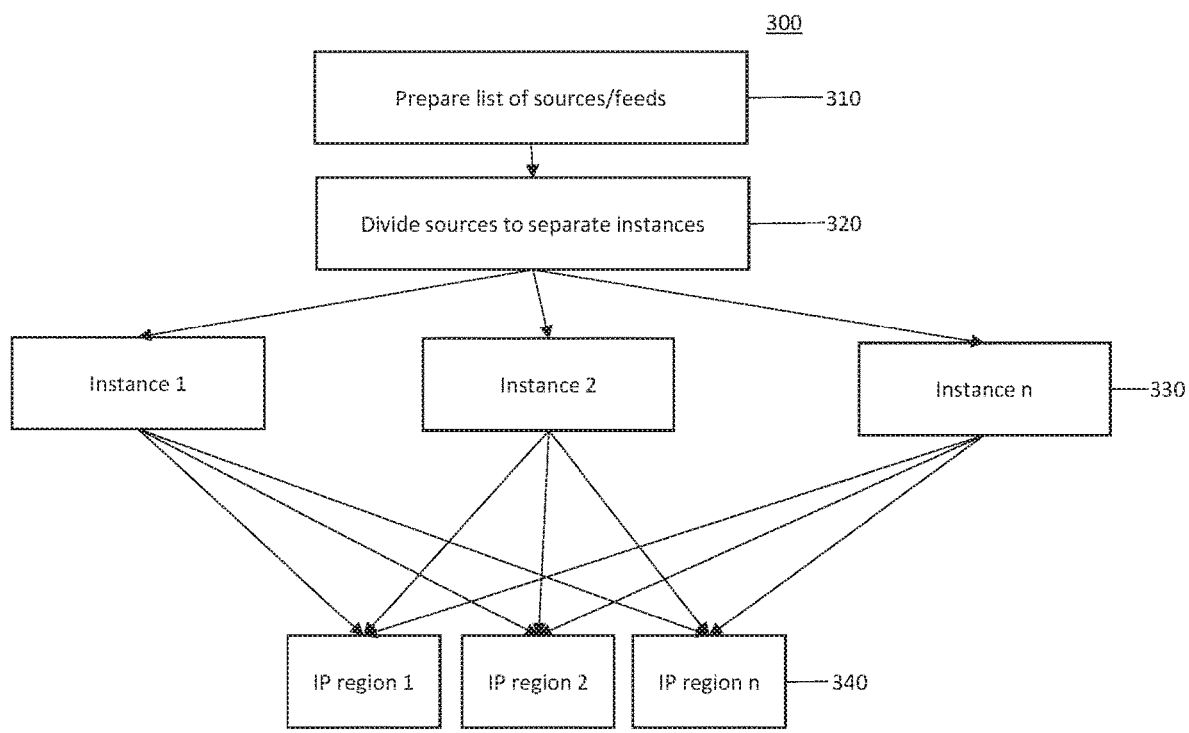
FIG. 3 is an example process associated with the disclosure of FIG. 2.

As shown in FIG. 3, a process 300 initializes a server-side crawler. The process 300 begins in step 310 by preparing a list of sources and/or feeds. For example, the list may include a set of sources representing a set of particular search categories. In step 320, the sources on the list are separated into multiple discrete instances 330, each having multiple discrete IP addresses 340. Thus, a crawling process may be spawned out to multiple physical servers and/or geographies to minimize being blocked by sources (e.g., research forums) for being a robotic searcher (e.g., bot). For example, the crawling process may be spread out over enough servers and geographies so that each source is only queried once per hour by any individual instance 330 having a specific IP address 340. As illustrated in FIG. 3, n instances 330 may be generated, where n is any whole number. Each instance 330 may have n IP regions 340, again where n is any whole number. For example, three instances 330 may be generated, each associated with three IP regions 340. The number of IP regions 340 may be independent of the number of instances 330, where the number of n instances 330 is different than the number of n IP regions.

Figure 4:
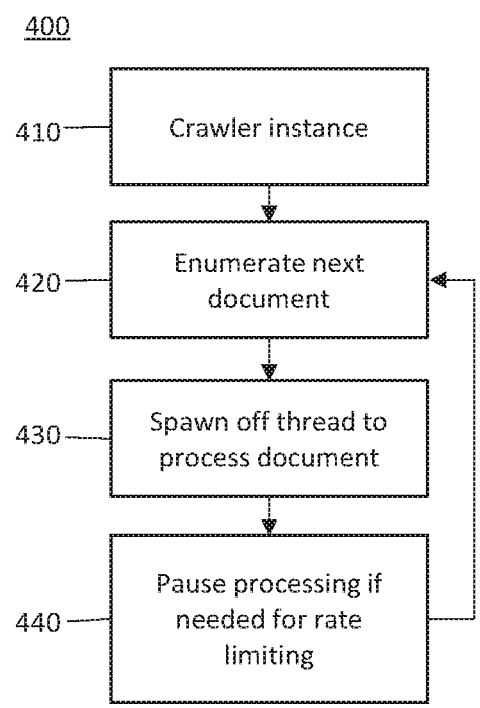
FIG. 4 is an example process associated with the disclosure of FIG. 2.

FIG. 4 illustrates a process 400 for implementing a crawler. In step 410 a crawling instance is generated. A next document is enumerated in step 420. In step 430 a separate thread is spawned off to process the enumerated document. This compartmentalizes processing overhead for any individual document to minimize or eliminate impacts to overall performance of the system. If necessary for rate limiting, the processing of the enumerated document is paused in step 440. The process 400 then returns to step 420 to enumerate and process a next document.

Figure 5:
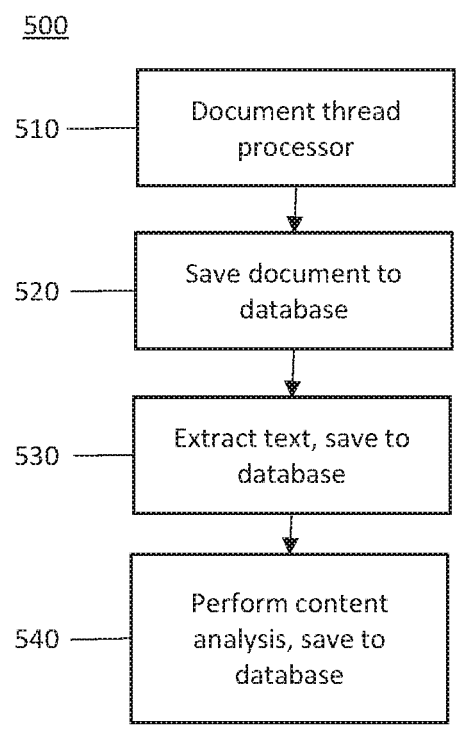
FIG. 5 is an example process associated with the disclosure of FIG. 2.

Process 500 shown in FIG. 5 illustrates a document processing flow. In step 510 a document thread processor is selected or initiated. For example, the document thread processor may receive the spawned thread from step 430 of process 400. A full copy of the document is downloaded and stored in a database (e.g., aggregated content database 234) in step 520. In step 530 raw text is extracted from the document and stored in the database. For example, the extracted text file may be stored in the aggregated content database 234, where it is cross-linked or associated with the original stored document. The extracted text is then analyzed and the results of the content analysis are stored in the database in step 540. For example, the extracted text may be analyzed and stored by the non-linguistic content analysis system referenced above. The stored results may be cross-linked or associated with the original stored document and/or the extracted text in the aggregated content database 234, for example.

Figure 6:
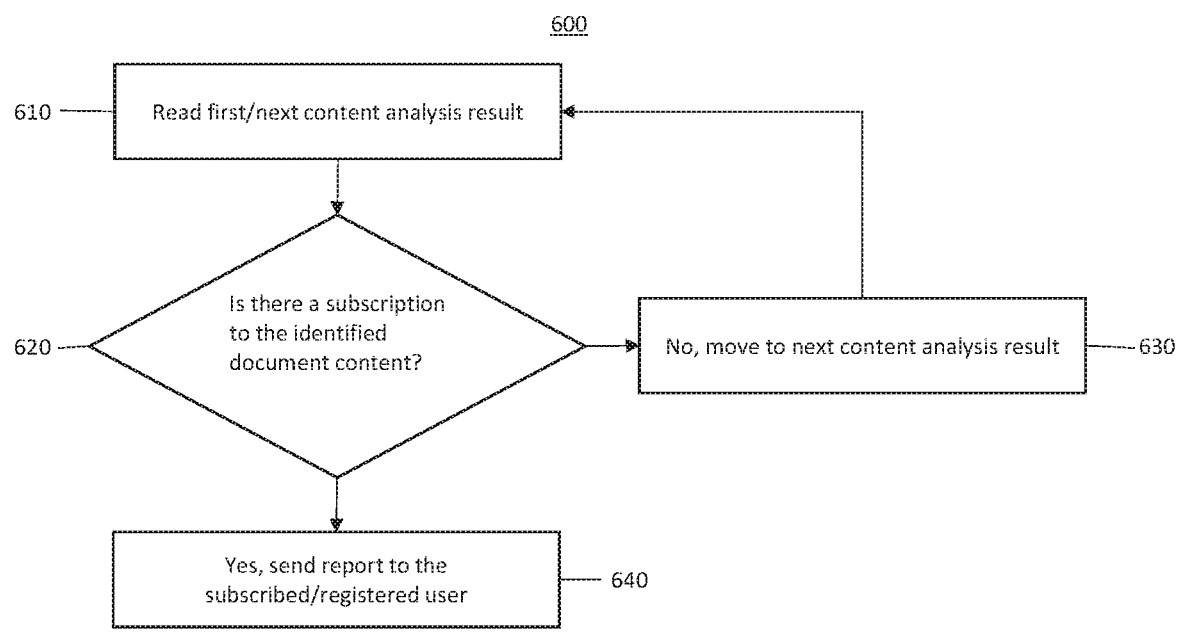
FIG. 6 is an example process associated with the disclosure of FIG. 2.

FIG. 6 illustrates a process 600 for providing relevant results to a registered user. In step 610 a first content analysis result is read. For example, the trigger/subscription monitoring and notification application 236 may read a content analysis result stored in aggregated content database 234. A determination is made whether there is a subscription to the identified document associated with the content analysis result in step 620. In step 630, if there is not a subscription to the identified document then the process returns to step 610 and reads a next content analysis result. If it is determined there is a subscription to the identified document, then a report is sent to the subscribed or registered user in step 640.

Figure 7:
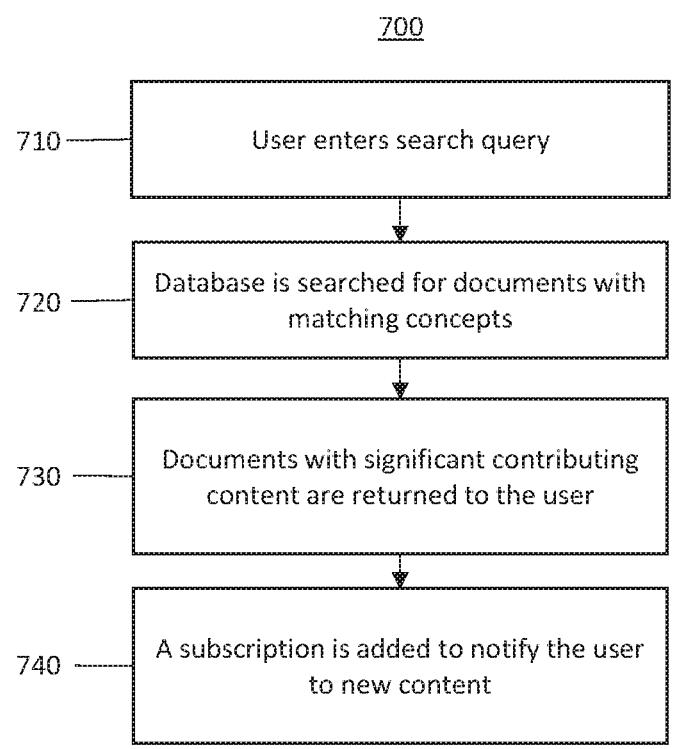
FIG. 7 is an example process associated with the disclosure of FIG. 2.

FIG. 7 illustrates a process 700 for providing relevant documents to a user. In step 710 the user enters a search query. For example, the search query may be entered on the user's client device 110 and sent via the network 150 to the relevant server 130. A database of aggregated content (e.g., aggregated content database 234) is searched for documents with matching concepts to the user inputs provided in the search query in step 720. In step 730 documents with significant contributing content are provided back to the user. For example, based on the user inputs, documents in the database may be ranked or weighted based on the degree of relevance such that only a specific number of documents with the highest rank/weight are returned to the user. In step 740 a subscription is added to notify the user to new content that becomes available on an ongoing basis, where the new content is again ranked/weighted in view of the user inputs. Thus, process 700 may establish an ongoing subscription based on the initial user query and continuously notify the user as new content that exceeds a threshold rank/weight is posted on any of the monitored sources or feeds.

Figure 8:
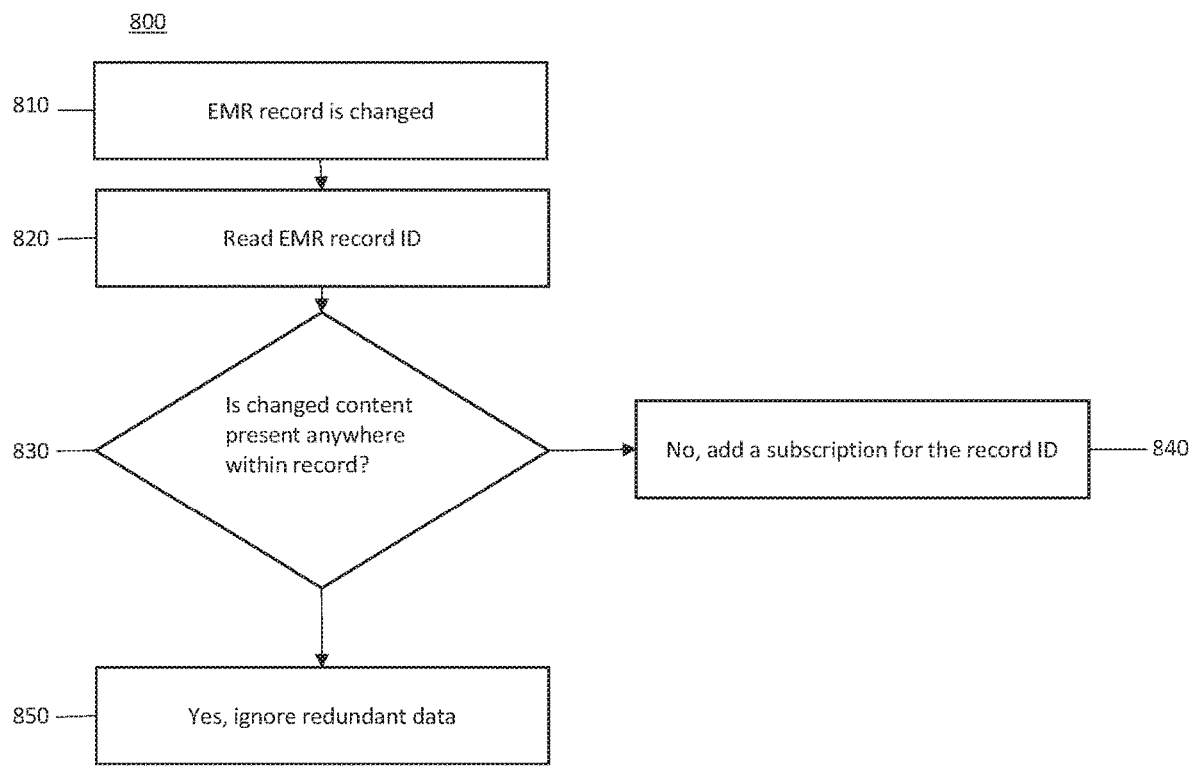
FIG. 8 is an example process associated with the disclosure of FIG. 2.

Process 800 illustrated in FIG. 8 provides for updating an EMR system with relevant content. In step 810 an EMR record is changed (e.g., new medical information entered by physician/nurse). An EMR record ID is read in step 820. In step 830 it is determined whether changed content is present within the record. If changed content is not present in the record, a subscription for the record ID is added in step 840. In step 850, if the changed content is present in the record, the redundant data is ignored.

An example will now be described using the example processes 300-700 of FIGS. 3-7, a client 110 that is a smartphone and having an output device 214 that is a flat panel display, an input device 216 that is a touch screen interface, a content item database 224 that stores content that can be displayed on the smartphone, and a communications module 218 that provides for communication between the smartphone client 110 and a network 150 of servers 130, with at least one server 130 having an aggregated content database 234 and a trigger/subscription monitoring and notification application 236.

In this example, a researcher working in the field of particle physics wants to keep up to date on papers pertinent to the researcher's work, which is more narrowly related to quarks. With a volume of hundreds of papers being published each week in particle physics, it is impractical to read and personally ingest all new content in the field of particle physics.

Here, the process begins when the trigger/subscription monitoring and notification application 236 on a server 130 generates an initial aggregation of content from a variety of sources and feeds using n instances each having n IP regions via processes 300, 400, 500. The initial aggregation of content is stored in the aggregated content database 234 and includes original documents, related extracted text documents, and related content analysis results. The trigger/subscription monitoring and notification application 236 may utilize parallel processors in server 130, processors of multiple servers 130 and/or clients 110 over network 150, or a combination of both.

Continuing the example, the trigger/subscription monitoring and notification application 236 executes process 700 by receiving a search query of "quarks" and the searcher's email address as input by the searcher on the searcher's client device 110, searching the initial aggregation of content, returning information on the most relevant content (e.g., strongly related to quarks) to the researcher's client device 110, and adding a subscription to notify the researcher when new content related to quarks is added to the sources, feeds and/or aggregated content database 234.

Some days later, a new paper is published on the arXiv pre-print server, for example. The trigger/subscription monitoring and notification application 236 downloads the new paper and identifies that it contains a significant quantity of content pertaining to quarks through content analysis. The trigger/subscription monitoring and notification application 236 checks for any active subscriptions to the word "quarks" within its database and identifies that the researcher wants to be notified of new content significantly pertaining to quarks. The trigger/subscription monitoring and notification application 236 sends an email to the supplied email address with a link to the full copy of the new paper and a text abstract within the email body, as well as an indication of other keywords in the paper (e.g., "gluons," "fermions," "protons"). The process continuously monitors the designated sources and feeds for newly posted content, continuing to send all new content significantly pertaining to quarks to the researcher until such time as the subscription is stopped or cancelled (e.g., by researcher's request).

In another example, a doctor at a popular medical practice sees twenty patients in one day with an overall patient load of 250 patients per year. The doctor makes time to visit some medical conferences to learn about new treatments, but due to the doctor's busy caseload it is impractical to obtain and read all newly published research and active studies in the doctor's field of practice. Further, the doctor's patients all have different prescriptions and some of these patients have medical histories stretching back many years. To tame the complexity of keeping up with active research, the doctor leverages the disclosed system in integration with the doctor's EMR system.

Thus, the subject technology specifically eliminates the need for the doctor to conduct continuous general research. For this example, as the doctor inputs new prescriptions/treatments, the new prescriptions/treatments are automatically copied to the system server, which adds the new prescriptions/treatments as subscriptions to be monitored against new research that is constantly being collected.

Continuing the example, a new study is published by an international research team that indicates that a particular combination of drugs isn't as safe as conventionally thought. These drugs happen to have been prescribed by this doctor and are currently subscribed to within the system, with records tying back to the relevant patients in question. The doctor then receives an alert informing the doctor of this new study and that the study impacts ten of his patients. Understanding the implications of the new study, the doctor then immediately instructs these ten patients to stop taking their prescriptions and to come back into the office to be re-screened for an alternative treatment regimen. Thus, the doctor only needs to review the new study in view of these specific ten patients, all of which is teed up for the doctor as soon as it is available without any addition research time required by the doctor.

In yet another example of the subject technology, a professional software developer graduated from university over a decade ago, but wants to tune up a skillset in machine learning. Because the software developer already has a fairly deep background in engineering, the software developer does not want to follow a rudimentary course or have to read redundant information and/or watch lengthy videos to understand the subject.

Instead, the software developer uses the subject system with a starting query of "machine learning." The system then extracts content it has downloaded from a variety of sources (e.g., from part of a Wikipedia page), starting with introductory information on the topic. The system includes some news articles pertaining to recent advances in the field that are identified as low in complexity but high in information density and relevant value. Then, the system follows up with excerpts from a variety of foundational papers on the subject, then moving into increasingly complex examples of the subject, and eventually pointing to source code repositories and deep academic examples of cutting edge research on the subject. Thus, the software developer did not need to follow an endless tree of information digging having questionable value, but instead was able to have the most relevant articles and content directly provided.

In a further example, a very large corporation has a significant repository of research spanning dozens of verticals and representing thousands of man-years of effort. However, much of this data is disorganized or in disparate locations. Thus, the corporation may utilize the subject technology to index the entire corporate file server.

Then a new project is started, requesting that the engineering organization build a new type of computer processor. None of the engineers know if there has been prior work on processors in their organization. Typically, the engineers would use a conventional search indexing system to find content written about processors within the company. Typically, the conventional system finds tens of thousands of documents, all referencing the word "processor," thus requiring significant labor to sort through and identify the most relevant documents that pertain to building processors as opposed to documents that simply mention processors.

Instead, the engineers use the subject system to search for relevant content. Here, the engineers find that many of the documents identified by the conventional system are not particularly relevant. However, the subject system all identifies that there are a small number of internal documents that relate to an unfinished processor project the corporation started years ago, thus significantly expediting their efforts.

The subject technology improves the performance of the server system and the network. For example, the original document is only downloaded once, thus eliminating server and network resources from having to obtain and download the same document multiple times based on new user inputs. Similarly, the extracted text file associated with the original document is also only generated once, thus eliminating server resources from having to re-analyze each content document as new queries are received.

Hardware Overview

Figure 9:
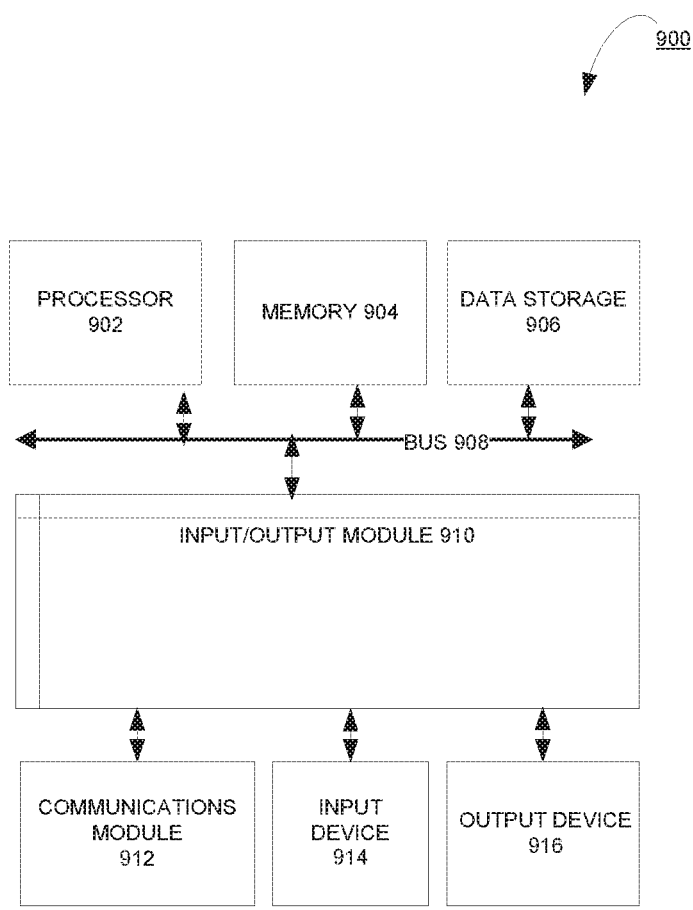
FIG. 9 is a block diagram illustrating an example computer system with which the clients and server of FIG. 2 can be implemented.

FIG. 9 is a block diagram illustrating an example computer system 900 with which the client 110 and server 130 of FIG. 2 can be implemented. In certain aspects, the computer system 900 may be implemented using hardware or a combination of software and hardware, either in a dedicated server or integrated into another entity or distributed across multiple entities.

Computer system 900 (e.g., client 110 or server 130) includes a bus 908 or other communication mechanism for communicating information, and a processor 902 (e.g., processor 212 and 236) coupled with bus 908 for processing information. According to one aspect, the computer system 900 is implemented as one or more special-purpose computing devices. The special-purpose computing device may be hard-wired to perform the disclosed techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques. By way of example, the computer system 900 may be implemented with one or more processors 902. Processor 902 may be a general-purpose microprocessor, a microcontroller, a Digital Signal Processor (DSP), an ASIC, a FPGA, a Programmable Logic Device (PLD), a controller, a state machine, gated logic, discrete hardware components, or any other suitable entity that can perform calculations or other manipulations of information.

Computer system 900 can include, in addition to hardware, code that creates an execution environment for the computer program in question, e.g., code that constitutes processor firmware, a protocol stack, a database management system, an operating system, or a combination of one or more of them stored in an included memory 904 (e.g., memory 220 and 230), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 908 for storing information and instructions to be executed by processor 902. The processor 902 and the memory 904 can be supplemented by, or incorporated in, special purpose logic circuitry. Expansion memory may also be provided and connected to computer system 900 through input/output module 910, which may include, for example, a SIMM (Single In Line Memory Module) card interface. Such expansion memory may provide extra storage space for computer system 900 or may also store applications or other information for computer system 900. Specifically, expansion memory may include instructions to carry out or supplement the processes described above and may include secure information also. Thus, for example, expansion memory may be provided as a security module for computer system 900 and may be programmed with instructions that permit secure use of computer system 900. In addition, secure applications may be provided via the SIMM cards, along with additional information, such as placing identifying information on the SIMM card in a non-hackable manner.

The instructions may be stored in the memory 904 and implemented in one or more computer program products, i.e., one or more modules of computer program instructions encoded on a computer readable medium for execution by, or to control the operation of, the computer system 900, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 904 may also be used for storing temporary variable or other intermediate information during execution of instructions to be executed by processor 902.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 900 further includes a data storage device 906 such as a magnetic disk or optical disk, coupled to bus 908 for storing information and instructions. Computer system 900 may be coupled via input/output module 910 to various devices. The input/output module 910 can be any input/output module. Example input/output modules 910 include data ports such as USB ports. In addition, input/output module 910 may be provided in communication with processor 902, so as to enable near area communication of computer system 900 with other devices. The input/output module 910 may provide, for example, for wired communication in some implementations, or for wireless communication in other implementations, and multiple interfaces may also be used. The input/output module 910 is configured to connect to a communications module 912. Example communications modules 912 (e.g., communications modules 218 and 238) include networking interface cards, such as Ethernet cards and modems.

The components of the system can be interconnected by any form or medium of digital data communication, e.g., a communication network. The communication network (e.g., network 150) can include, for example, any one or more of a PAN, a LAN, a CAN, a MAN, a WAN, a BBN, the Internet, and the like. Further, the communication network can include, but is not limited to, for example, any one or more of the following network topologies, including a bus network, a star network, a ring network, a mesh network, a star-bus network, tree or hierarchical network, or the like.

For example, in certain aspects, communications module 912 can provide a two-way data communication coupling to a network link that is connected to a local network. Wireless links and wireless communication may also be implemented. Wireless communication may be provided under various modes or protocols, such as GSM (Global System for Mobile Communications), Short Message Service (SMS), Enhanced Messaging Service (EMS), or Multimedia Messaging Service (MMS) messaging, CDMA (Code Division Multiple Access), Time division multiple access (TDMA), Personal Digital Cellular (PDC), Wideband CDMA, General Packet Radio Service (GPRS), or LTE (Long-Term Evolution), among others. Such communication may occur, for example, through a radio-frequency transceiver. In addition, short-range communication may occur, such as using a BLUETOOTH, WI-FI, or other such transceiver.

In any such implementation, communications module 912 sends and receives electrical, electromagnetic or optical signals that carry digital data streams representing various types of information. The network link typically provides data communication through one or more networks to other data devices. For example, the network link of the communications module 912 may provide a connection through local network to a host computer or to data equipment operated by an Internet Service Provider (ISP). The ISP in turn provides data communication services through the world wide packet data communication network now commonly referred to as the Internet. The local network and Internet both use electrical, electromagnetic or optical signals that carry digital data streams. The signals through the various networks and the signals on the network link and through communications module 912, which carry the digital data to and from computer system 900, are example forms of transmission media.

Computer system 900 can send messages and receive data, including program code, through the network(s), the network link and communications module 912. In the Internet example, a server might transmit a requested code for an application program through Internet, the ISP, the local network and communications module 912. The received code may be executed by processor 902 as it is received, and/or stored in data storage 906 for later execution.

In certain aspects, the input/output module 910 is configured to connect to a plurality of devices, such as an input device 914 (e.g., input device 216) and/or an output device 916 (e.g., output device 214). Example input devices 914 include a stylus, a finger, a keyboard and a pointing device, e.g., a mouse or a trackball, by which a user can provide input to the computer system 900. Other kinds of input devices 914 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 916 include display devices, such as a LED (light emitting diode), CRT (cathode ray tube), LCD (liquid crystal display) screen, a TFT LCD (Thin-Film-Transistor Liquid Crystal Display) or an OLED (Organic Light Emitting Diode) display, for displaying information to the user. The output device 916 may comprise appropriate circuitry for driving the output device 916 to present graphical and other information to a user.

According to one aspect of the present disclosure, the client 110 and server 130 can be implemented using a computer system 900 in response to processor 902 executing one or more sequences of one or more instructions contained in memory 904. Such instructions may be read into memory 904 from another machine-readable medium, such as data storage device 906. Execution of the sequences of instructions contained in main memory 904 causes processor 902 to perform the process steps described herein. One or more processors in a multi-processing arrangement may also be employed to execute the sequences of instructions contained in memory 904. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components.

Computing system 900 can include clients and servers. A client and server are generally remote from each other and typically interact through a communication network. The relationship of client and server arises by virtue of computer programs running on the respective computers and having a client-server relationship to each other. Computer system 900 can be, for example, and without limitation, a desktop computer, laptop computer, or tablet computer. Computer system 900 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer-readable medium" as used herein refers to any medium or media that participates in providing instructions or data to processor 902 for execution. The term "storage medium" as used herein refers to any non-transitory media that store data and/or instructions that cause a machine to operate in a specific fashion. Such a medium may take many forms, including, but not limited to, non-volatile media, volatile media, and transmission media. Non-volatile media include, for example, optical disks, magnetic disks, or flash memory, such as data storage device 906. Volatile media include dynamic memory, such as memory 904. Transmission media include coaxial cables, copper wire, and fiber optics, including the wires that comprise bus 908. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter affecting a machine-readable propagated signal, or a combination of one or more of them.

As used in this specification of this application, the terms "computer-readable storage medium" and "computer-readable media" are entirely restricted to tangible, physical objects that store information in a form that is readable by a computer. These terms exclude any wireless signals, wired download signals, and any other ephemeral signals. Storage media is distinct from but may be used in conjunction with transmission media. Transmission media participates in transferring information between storage media. For example, transmission media includes coaxial cables, copper wire and fiber optics, including the wires that comprise bus 908. Transmission media can also take the form of acoustic or light waves, such as those generated during radio-wave and infra-red data communications. Furthermore, as used in this specification of this application, the terms "computer", "server", "processor", and "memory" all refer to electronic or other technological devices. These terms exclude people or groups of people. For the purposes of the specification, the terms display or displaying means displaying on an electronic device.

In one aspect, a method may be an operation, an instruction, or a function and vice versa. In one aspect, a clause or a claim may be amended to include some or all of the words (e.g., instructions, operations, functions, or components) recited in either one or more clauses, one or more words, one or more sentences, one or more phrases, one or more paragraphs, and/or one or more claims.

To illustrate the interchangeability of hardware and software, items such as the various illustrative blocks, modules, components, methods, operations, instructions, and algorithms have been described generally in terms of their functionality. Whether such functionality is implemented as hardware, software or a combination of hardware and software depends upon the particular application and design constraints imposed on the overall system. Skilled artisans may implement the described functionality in varying ways for each particular application.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

To the extent that the term "include," "have," or the like is used in the description or the claims, such term is intended to be inclusive in a manner similar to the term "comprise" as "comprise" is interpreted when employed as a transitional word in a claim. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects can be implemented and are within the scope of the following claims. For example, while operations are depicted in the drawings in a particular order, this should not be understood as requiring that such operations be performed in the particular order shown or in sequential order, or that all illustrated operations be performed, to achieve desirable results. The actions recited in the claims can be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A computer-implemented method for providing instrumented research aggregation results, the method comprising:
   providing, to one or more servers, a set of content sources;
   initiating, by the one or more servers, a plurality of crawling instances, each crawling instance associated with a plurality of Internet Protocol (IP) addresses;
   generating, on the one or more servers, an aggregated content database based on the plurality of crawling instances;
   identifying, by a first crawling instance, a new content document on a first content source, wherein the new content document is newly published and is not currently in the aggregated content database;
   downloading and storing in the aggregated content database, by the one or more servers, a copy of the new content document and a link back to the original new content document on the first content source;
   extracting, by the one or more servers, substantially all text content from the new content document;
   storing, in the aggregated content database, the extracted text content as a text document, wherein the text document is associated with the new content document;
   executing, by the one or more servers, a content analysis of the text document;
   storing, in the aggregated content database, content analysis results of the content analysis, wherein the content analysis results are associated with the text document representing the new content document; and
   providing initial information related to the new content document based on one or more user inputs and the content analysis results;
   wherein one of the set of content sources is an electronic medical record (EMR) system and the method further comprises:
   comparing newly entered patient treatment data for a first EMR record against previously collected treatment data for the first EMR record;
   generating a query to the one or more servers if the newly entered patient treatment data does not match any of the previously collected data, the query including a plaintext string and an identifier for the first EMR record;
   automatically generating a subscription for the plaintext string; and
   providing the link to the new content document and the first EMR record identifier if a concept identified from the content analysis matches the subscribed plaintext string.

2. The method of claim 1, wherein the aggregated content database comprises a plurality of content documents, a plurality of text documents and a plurality of content analysis results, each content document being associated with one of the plurality of text documents and one of the plurality of content analysis results.

3. The method of claim 1, wherein two or more of the plurality of crawling instances share one or more of the IP addresses.

4. The method of claim 1, wherein the first content source includes a Rich Site Summary (RSS) feed and the RSS feed is the basis for identifying when content is published.

5. The method of claim 1, wherein the identifying the new content document includes checking a timestamp of a file repository.

6. The method of claim 1, wherein the identifying the new content document includes incrementing an index of a file name.

7. The method of claim 1, wherein the identifying the new content document includes downloading webpage content and comparing it against previously downloaded content to identify differences.

8. The method of claim 1, wherein a plurality of new content documents are downloaded and stored in the aggregated content database, and wherein each of the plurality of new content documents are passed into a separate thread for asynchronous processing.

9. The method of claim 1, further comprising:
   iterating over output from the content analysis of the text document; and
   comparing iteration results against a database of user-supplied trigger concepts.

10. The method of claim 9, further comprising:
    sending a notification to a first user if an identified concept in the new content document matches one of the user-supplied trigger concepts.

11. The method of claim 10, wherein the notification comprises one of an email, a text message, and an output on a dashboard.

12. The method of claim 1, wherein the provided initial information related to the new content document includes the link back to the original new content document and a portion of an abstract of the new content document.

13. The method of claim 1, wherein the set of content sources represents a superset of available research categories.

14. The method of claim 1, further comprising:
receiving a query comprising one of a keyword and a phrase;
identifying, in the aggregated content database, a threshold number of content documents having the highest correlation to the query;
identifying, from the highest correlated content documents, topics related to the query;
identifying the most relevant portions of the highest correlated content documents based on the query and the related topics; and
presenting the identified most relevant portions in order of least complex to most complex.

15. A non-transitory machine-readable storage medium comprising machine-readable instructions for causing a processor to execute a method for providing instrumented research aggregation results, the method comprising:
generating an aggregated content database based on a plurality of crawling instances, wherein the aggregated content database comprises a plurality of content documents, a plurality of text documents and a plurality of content analysis results, each content document being associated with one of the plurality of text documents and one of the plurality of content analysis results;
identifying, by a first crawling instance, a new content document on a first content source, wherein the new content document is newly published and is not currently in the aggregated content database;
downloading and storing in the aggregated content database a copy of the new content document and a link back to the original new content document on the first content source;
generating a text document from the new content document;
storing, in the aggregated content database, the text document, wherein the text document is associated with the new content document;
performing content analysis of the text document;
storing, in the aggregated content database, content analysis results from the content analysis, wherein the content analysis results are associated with the new content document; and
providing initial information related to the new content document based on one or more user inputs;
wherein the plurality of content documents is an electronic medical record (EMR) system and the method further comprises:
comparing newly entered patient treatment data for a first EMR record against previously collected treatment data for the first EMR record;
generating a query to the aggregated content database if the newly entered patient treatment data does not match any of the previously collected data, the query including a plaintext string and an identifier for the first EMR record;
automatically generating a subscription for the plaintext string; and
providing the link to the new content document and the first EMR record identifier if a concept identified from the content analysis matches the subscribed plaintext string.

16. The non-transitory machine-readable storage medium of claim 15, wherein generating the aggregated content database comprises:
providing a set of content sources representing a superset of available research categories;
initiating a plurality of crawling instances, each crawling instance associated with a plurality of Internet Protocol (IP) addresses, wherein two or more of the plurality of crawling instances share one or more of the IP addresses;
downloading and storing a plurality of content documents identified by the plurality of crawling instances;
passing each of the plurality of content documents into a separate thread for asynchronous processing; and
storing, for each of the plurality of content documents, an associated text file and associated content analysis results generated from the separate processing thread.

* * * * *